(12) United States Patent
Beatrix (10) Patent No.: US 10,751,042 B2
(45) Date of Patent: Aug. 25, 2020

(54) SKIN EXPANSION SYSTEM

(71) Applicant: MEDICAL INNOVATION DEVELOPPEMENT, Dardilly (FR)

(72) Inventor: Olivier Beatrix, Lyons (FR)

(73) Assignee: MEDICAL INNOVATION DEVELOPPEMENT, Dardilly (FR)

( * ) Notice: Subject to any disclaimer, the term of this patent is extended or adjusted under 35 U.S.C. 154(b) by 0 days.

(21) Appl. No.: 15/548,459

(22) PCT Filed: Feb. 5, 2016

(86) PCT No.: PCT/FR2016/050257
§ 371 (c)(1),
(2) Date: Aug. 3, 2017

(87) PCT Pub. No.: WO2016/124872
PCT Pub. Date: Aug. 11, 2016

(65) Prior Publication Data
US 2018/0021037 A1 Jan. 25, 2018

(30) Foreign Application Priority Data
Feb. 6, 2015 (FR) ...................................... 15 50937

(51) Int. Cl.
*A61B 17/04* (2006.01)
*A61B 90/00* (2016.01)

(52) U.S. Cl.
CPC ...... *A61B 17/0466* (2013.01); *A61B 17/0401* (2013.01); *A61B 17/0487* (2013.01);
(Continued)

(58) Field of Classification Search
CPC .......... A61B 17/0466; A61B 2017/081; A61B 2017/086; A61B 2017/088; A61B 90/02; A61B 17/0401; A61B 17/0487
See application file for complete search history.

(56) References Cited

U.S. PATENT DOCUMENTS 4,210,148 A * 7/1980 Stivala ............... A61B 17/0466
606/232
6,471,715 B1 * 10/2002 Weiss ..................... A61B 17/04
606/216

(Continued)

FOREIGN PATENT DOCUMENTS

EP 0592960 4/1994
EP 1852071 11/2007
(Continued)

*Primary Examiner* — Tuan V Nguyen
(74) *Attorney, Agent, or Firm* — Clark & Brody LP (57) ABSTRACT

A skin expansion system (1) for reducing a wound surrounded by tissue, the skin expansion system (1) comprising; an elastically deformable tie (5) intended to extend between the tissues surrounding the wound in such a way that tension in the tie (5) produces traction along the tissues surrounding the wound in order to bring said tissues closer together, the tie (5) having first (5a) and second opposing ends, a tensioner (10) suitable for maintaining tension in the tie (5), in which the tie (5) is suitable for suturing the wound by passing directly through the tissues surrounding the wound in at least two suturing points, the tie being made from a biocompatible material and comprising a suture needle (6) rigidly connected to the first end (5a).

10 Claims, 5 Drawing Sheets

(52) U.S. Cl.
CPC ...... *A61B 90/02* (2016.02); *A61B 2017/0404* (2013.01); *A61B 2017/0406* (2013.01); *A61B 2017/0414* (2013.01); *A61B 2017/0464* (2013.01); *A61B 2017/0496* (2013.01)

(56) References Cited

U.S. PATENT DOCUMENTS

| | | | |
|---|---|---|---|
| 2003/0092969 A1 | 5/2003 | O'Malley et al. | |
| 2004/0260344 A1 | 12/2004 | Lyons et al. | |
| 2006/0009803 A1* | 1/2006 | Garay | A61B 17/0401 606/217 |
| 2006/0064125 A1* | 3/2006 | Henderson | A61B 17/02 606/215 |
| 2011/0040325 A1 | 2/2011 | Moehrle | |
| 2012/0016384 A1 | 1/2012 | Wilke et al. | |

FOREIGN PATENT DOCUMENTS

| | | |
|---|---|---|
| JP | 2013-094409 | 5/2013 |
| JP | 2014-217633 | 11/2014 |
| WO | 99/35974 | 7/1999 |
| WO | 2013/134767 | 9/2013 |

\* cited by examiner

SKIN EXPANSION SYSTEM

FIELD OF THE INVENTION

The invention relates to a skin expansion system.

In particular, the invention relates to a skin expansion system of the vessel loop closure type using an external tissular extension by an elastic tie to reduce the size of a wound by applying traction along tissues surrounding the wound. External tissular extension by elastic tie is known and was disclosed several decades ago, particularly in the following publications:

BACKGROUND OF THE DISCLOSURE

Harris I, "Gradual closure of fasciotomy wounds using a vessel loop shoelace", Injury 1993; 24(8): 565-6,
Asgari M M, Spinelli H M, "The vessel loop shoelace technique for closure of fasciotomy wounds", Ann Plast Surg 1999; 43: 225-9,
Bashir A H, "Wound closure by skin traction: an application of tissue expansion", Br J Plast Surg 1987; 40(6): 582-7,
Bulstrode C J, "A simple method for closing fasciotomies", Ann R Col Surg Engl 1985; 67(2): 119-20,
Almekinders L C, "Gradual closure of fasciotomy", Orthop Rev 1991; 20(1): 82-4,
Monnier J, "Extension tissulaire uni-axiale dans la couverture des pertes de substance des membres" (Uniaxial tissular extension in the coverage of limb substance loss), Annal chir plast 52 (2007): 577-581.

This technique uses elastic properties of the skin in particular, and consists in applying progressive tension on two edges of the skin around the wound when a direct suture is impossible due to loss of substance, excessive tension between the two skin edges or during discharge aponevrotomies made in the case of a compartment syndrome. A compartment syndrome is defined as a neuromuscular complaint that can lead to necrosis, related to an increase in the intratissular pressure in an inextensible muscular compartment. It is secondary to trauma or ischemia. The only way of reducing the pressure in the compartment is to open it widely. This action is done is vascular surgery or orthopaedic surgery and can save the muscle concerned and its function, but it causes a large skin gap equivalent to a loss of substance.

Therefore the invention is applicable to the treatment of a long wound with a surface area of between 100 cm2 and 500 cm2 and for example resulting from a aponevrotomy operation or ablation of a skin tumour. The invention is also applicable to the treatment of a smaller wound, for example with an area of less than 100 cm2, for example resulting from a post-operational disunion.

The principle of external tissular extension is to apply progressive traction on the two skin edges to bring them together and ideally to bring them into contact such that the wound is completely closed. The skin expansion system is put into place at the end of the operation. The progressive traction is generally applied immediately after the operation (second day after the operation) and is continued for about fifteen days. Traction is increased at the patient's bed every forty-eight hours. The skin expansion system is removed without anaesthetic.

At the present time, this technique is applied using standard equipment not used in the way it was intended, and particularly by:

a silicone loop as an elastically deformable tie intended to extend between the tissues surrounding the wound such that a tension in the tie creates traction along the tissues surrounding the wound to bring said tissues towards each other, the silicon loop is then not used as it was intended which is per-operational marking of vascular or noble structures (ureter, bile duct),
staples usually used for closing the skin at the end of an operation,
a tensioner adapted to maintain tension in the tie.

The tie in this known skin expansion system passes in sequence through the staples, anchored through the tissues surrounding the wound. The tie is then held in tension by the tensioner, for example in the form of a cleat on one or several staples.

However, although very widespread and ethical because it is used in a rescue situation in which there is no alternative solution, the skin extension technique making use of medical equipment designed for other purposes often has disappointing results.

In particular, the known skin expansion system is long and complex to implement due to the need to start by anchoring staples along the tissues surrounding the wound. Furthermore, in this known skin expansion system, traction on the tissues surrounding the wound is applied through staples and depends on the anchorage of each staple. Despite the care taken in anchoring staples, they do not allow controlled traction, particularly along an appropriate direction. Therefore the known skin expansion system cannot apply uniform traction along the tissues surrounding the wound. There is then a risk of damage or even necrosis of the tissues, at least locally and particular at the locations at which tension is highest. Furthermore, staples diverted from their normal use do not have any particular mechanical properties and there is a risk of them tearing out.

Other examples of a skin expansion system according to the preamble of claim 1 are described in documents US 2012/0016384 and US 2003/0092969. However, due to the envisaged anchors, these skin expansion systems create a serious risk of damaging or even tearing tissues surrounding the wound.

The invention aims to mitigate the problems mentioned above.

SUMMARY OF THE DISCLOSURE

To achieve this, the invention discloses a skin expansion system to reduce a wound surrounded by tissues, the skin expansion system comprising:
an elastically deformable tie intended to extend between the tissues surrounding the wound in such a way that tension in the tie produces traction along the tissues surrounding the wound in order to bring said tissues closer together, the tie having opposed first and second ends, the tie having at rest a length between the first and second ends and being elastically stretchable to move the first and second ends away from each other,
a tensioner adapted to maintain tension in the tie,
wherein the tie is adapted to suture the wound by passing directly through the tissues surrounding the wound at at least two suture points, the tie being made of a biocompatible material and comprising a suture needle fixed to the first end, the skin expansion system also comprising at least one spacer intended to be inserted between the tie and the tissues surrounding the wound, the spacer having a bearing surface adapted to rest on the tissues surrounding the wound, and a guide surface opposite the bearing surface adapted to receive a portion of the tie.

Thus, the tie forming a direct suture of the wound can be placed easily and simply by an action intuitive for a surgeon. Furthermore, the traction applied by the elastically deformable tie directly on the skin can be better distributed between the suture points and more uniformly along the tissues surrounding the wound such that the risks of damage and necrosis are reduced. This protection of the tissues surrounding the wound against risks of damage and necrosis is improved by the combination of the elastically extendible tie with one or several spacers transferring tension applied on the tissues surrounding the wound by an extended surface area corresponding to the bearing area. In particular, when tension is applied to the tie in order to close the wound, the traction on the tissues can be applied progressively, due to the stretching of the tie and distributed by the bearing of the spacer. The spacers can also improve guidance of the tie and facilitate its placement.

The skin expansion system according to this invention has the following advantages in particular
  firm anchorage to the skin so that the procedure can be completed,—skin protection capable of applying traction without damaging the skin,
  development of a reversible locking system that can easily be used on the elastic loop,—good ergonomics facilitating placement, manipulation and ablation,—a reliable system to maximise safety of the patient.

It provides an improvement to the medical service provided, to consolidate existing classical indications of the external skin extensions technique and particularly:
  in vascular surgery, to close discharge aponevrotomies following a post-ischemia compartments syndrome,
  in orthopaedic surgery, to close discharge aponevrotomies following a post-trauma and/or ischemia compartments syndrome,
  in oncological surgery (cancerology) to close large losses of skin and sub-cutaneous substances.

The skin expansion system according to the invention also has sufficient adaptability to extend indications of the external skin extension technique to new indications, such as:
  reduction of the area to be grafted after resection of a small tumour or extended work on the treatment of melanoma,
  post-operative healing disunions.

The tie may be made of polymer, and particularly silicone.
The tensioner may comprise:
  a body fixed to the second end of the tie, and
  a blocking device that can be moved relative to the body between an inactive state in which said blocking device releases a passage for the tie between a blocking portion of said blocking device and the body, and an active state in which said blocking device keeps a portion of the tie at a distance from the second end between the blocking portion of said blocking device and the body.

Such a spacer could be used independently of the skin expansion system as defined above for any other application making use of a suture, with any appropriate type of tie possibly different from the tie defined above.

The bearing surface may be deprived from an anchor member adapted to pierce the tissues surrounding the wound and penetrate into said tissues.

The spacers then do not form an anchor point, the anchor point being composed of the tie suture point through the tissues.

The guide surface can extend along a guide axis and can be concave around the guide axis.

The spacer can comprise at least one guide opening with a lateral surface around a central axis and adapted to enable the tie to pass through, the lateral surface forming at least part of the guide surface.

The spacer can comprise at least two guide openings separated from each other by a break-off portion.

The spacer may be made of polymer, and particularly silicone. These provisions make it possible to adapt the spacer to the anatomy of the tissues on which it lies.

According to another aspect, the invention relates to a method of reducing a wound surrounded by tissues using a skin expansion system as defined above, the method of reducing a wound including steps consisting of:
  suture the wound by passing directly through the tissues surrounding the wound at at least two suture points with the tie such that the tie extends between the tissues surrounding the wound,
  apply tension in the tie so as to create traction in the tissues surrounding the wound to bring said tissues towards each other,
  maintain the tension in the tie using the tensioner.

The method or reducing a wound can also adjust and particularly increase the tension in the tie.

The method of reducing a wound can include insertion of at least one spacer between the tie and the tissues surrounding the wound during the step in which the wound is sutured, the spacer having a bearing area resting on the tissues surrounding the wound, and a guide surface opposite the bearing surface and receiving a portion of the tie.

BRIEF DESCRIPTION OF THE DRAWINGS

Other purposes and advantages of the invention will become clear after reading the following description of a particular embodiment of the invention given as a non-limitative example, with reference to the appended drawings among which.

DETAILED DESCRIPTION OF THE INVENTION

On the figures, the same references denote identical or similar elements.

Figures 1, 2:
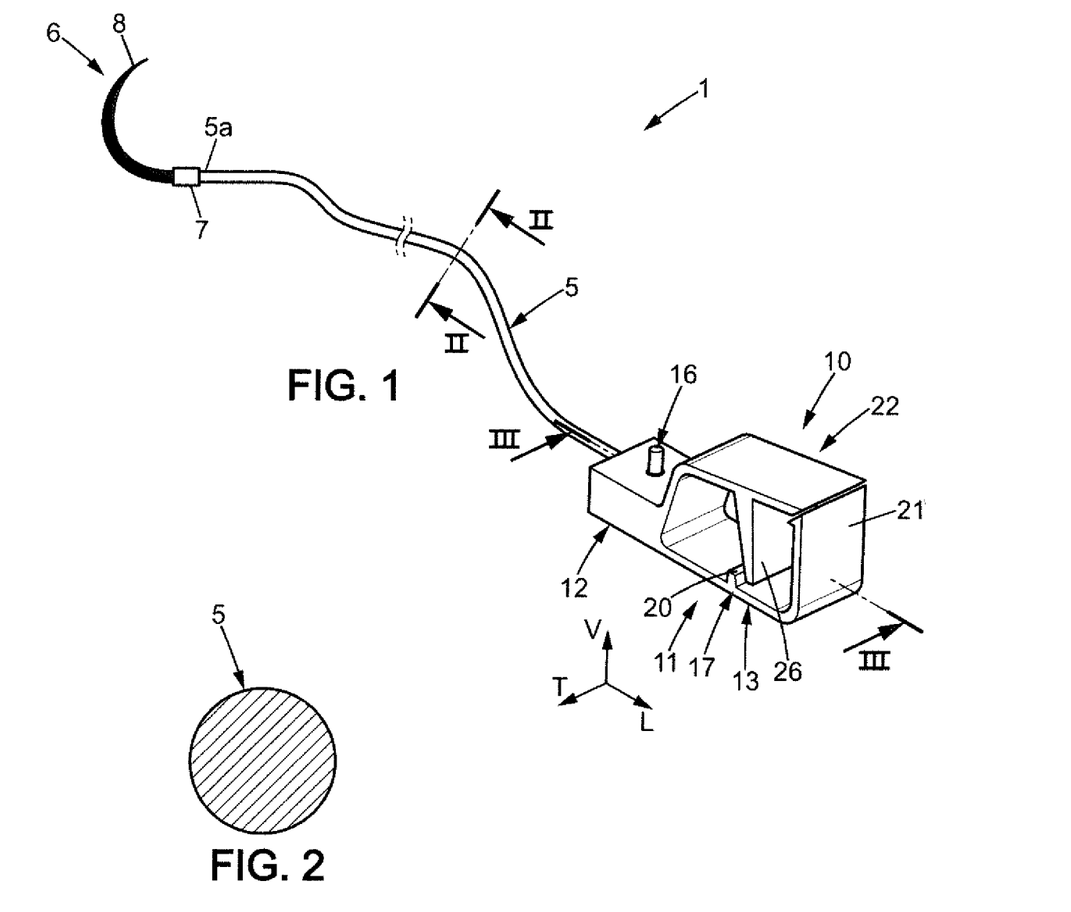
FIG. 1 is a perspective view of a skin expansion system according to one embodiment of the invention, the skin expansion system including a tie adapted to suture the wound, a suture needle fixed to a first end of the tie and a tensioner fixed to a second end of the tie.
FIG. 2 is a sectional view along the direction reference II-II on FIG. 1 of the tie of the skin expansion system of FIG. 1.
Figure 3:
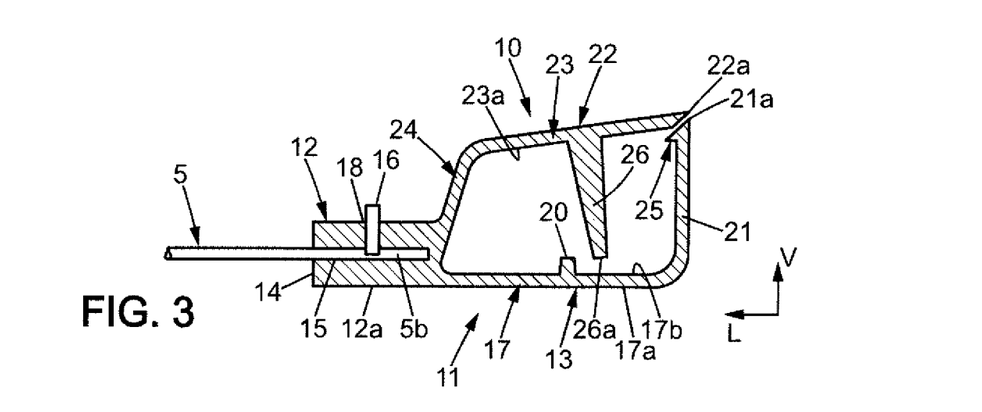
FIG. 3 is a sectional view along the direction reference III-III on FIG. 1 of the tensioner of the skin expansion system tensioner of FIG. 1, FIGS. 4 and 5 are perspective and elevation views respectively of a variant of the tensioner of the skin expansion system of FIG. 1.

FIGS. 1 to 3 represent a skin expansion system 1 to reduce a wound 2 surrounded by tissues 3. The skin expansion system 1 is of the vessel loop closure type in which the wound 2 is reduced by applying traction along the tissues 3 surrounding the wound 2.

The skin expansion skin I comprises a tie 5 adapted to suture the wound 2 passing directly through the tissues 3 surrounding the wound at several suture points 4. In particular, the tie 5 is made of a biocompatible and elastically deformable material, particular elastically extensible, such as silicone. The tie 5 at rest, in other words when there is no external constraint, has a length between opposite first 5a and second 5b ends, and it can be stretched to move the first part 5a and the second end 5b away from each other. In particular, the length of the tie 5 can be between 20 cm and 80 cm, and preferably between 40 cm and 60 cm. The tie 5 may be provided with a graduation over its entire length.

On FIG. 2, the tie 5 is shown with a circular cross-section with a diameter of between 1 and 3 mm. As a variant, the tie 5 can have any other non-circular cross-section and present, for example, first and second dimensions along first D1 and second D2 directions perpendicular to each other such that the first dimension is larger than the second dimension. In particular, the tie could have an oval cross-section with a major axis a along the first direction D1 and a minor axis b along the second direction D2.

The tie 5 also comprises a suture needle 6 fixed to its first end 5a. For example, the suture needle 6 can be curved and can be crimped at the first end 5a of the tie 5. A ring 7, fixed to an end opposite a tip 8 of the suture needle 6 and adapted to receive the first end 5a of the tie 5, is then deformed to retain the tie 5 inside the ring 7. To be able to separate the suture needle 6 from the tie 5 once the suture has been made, one of the elements, chosen among the tie 5 or the suture needle 6 can include a break-off portion. In particular, due to the nature of the material of the tie 5, the tie can be cut close to the suture needle 6. As a variant, the suture needle 6 can be fixed to the first end Sa of the tie 5 by any appropriate means and particularly by force fitting, overmoulding or through any appropriate and possibly removable attachment means.

The second end 5b of the tie 5 is fixed to a tensioner 10 adapted to maintain tension in the tie 5.

In the embodiment shown on FIGS. 1 and 3, the tensioner 10 comprises a body 11 that extends along a longitudinal direction L between a distal part 12 to which the tie 5 is fixed, and a proximal part 13.

The distal part 12, for example parallelepiped shaped, has a transverse end 14 relative to the longitudinal direction L and provided with an orifice 15 that extends along an axis and that is adapted to house the second end 5b of the tie 5.

The second end 5b of the tie 5 is held in the orifice 15 by a tightening device 16 installed in a hole 18 on a top surface of the distal part 12 of the body 11 so as to be moveable perpendicular to the axis of the orifice 15. The tightening device 16 can then be moved between:
- a tightening position in which a part of the tightening device 16 extends in the orifice 15 so as to trap the tie 5 between one end of the tightening device 16 and a lateral surface of the orifice 15, and
- a retracted position in which the tightening device 16 does not extend in the orifice 15 so as to not interfere with the tie 5.

As a variant, the second end 5b of the tie 5 could be held in the orifice 15 by any other appropriate means.

The proximal part 13 extends along the longitudinal direction L from a surface opposite the end surface 14 of the distal part 12. It is added along a transverse direction T, perpendicular to the longitudinal direction L. In particular, it comprises a bottom wall 17, a lower surface 17a of which forms a prolongation of a lower surface 12a of the distal part 12. The base wall 17 comprises, on a top surface 17b opposite the bottom surface 17a, a projection 20 that extends over its entire width measured along the transverse direction T. The proximal part 13 also includes a cross-wall 21 that extends perpendicular to the longitudinal direction L, along a vertical direction V from one end of the bottom wall 17 opposite the distal part 12.

The tensioner 10 also comprises a blocking device made in the form of a blocking lever 22 adapted to reversibly block a portion of the tie 5 at a distance from the second end 5b.

In the embodiment shown, the blocking lever 22 is made in one piece with the body 1 made of a plastic material. The blocking lever 22 is also shaped such that, when at rest without any external forces being applied, a free end 22a of the blocking lever 22 is placed close to a free end 21a of the transverse wall 21 of the proximal part 13 of the body 1.

In particular, the blocking lever 22 comprises a blocking wall 23 arranged to be approximately facing the bottom wall 17 of the proximal part 13, and including the free end 22a of the blocking lever 22. The blocking wall 23 is connected to the distal part 12 by a connecting wall 24 approximately perpendicular to the longitudinal direction L. When at rest, the blocking lever 22 is in an open position corresponding to an inactive state in which its free end 22a is close to the free end 21a of the transverse wall 21 of the proximal part 13 of the body 11, forming a passage for the tie 5.

The blocking lever 22 can be elastically deformed to move towards a closed position corresponding to an active state in which it holds a portion of the tie 5 at a distance from the second end 5b between its free end 22a forming a blocking portion and the free end 21a of the cross wall 21 of the proximal part 13 of the body 11. The free end 21a of the cross wall 21 of the proximal part 13 of the body 11 is then fitted with a stud 25 to hold the blocking lever 22 in the active state, in the closed position.

The blocking lever 22 comprises a blocking tab 26 that extends perpendicular from a lower surface 23a of the blocking wall 23 facing the top surface 17b of the bottom wall 17 of the proximal part 13 of the body 11. The blocking tab 26 is arranged such that:
- in the open position of the blocking lever 22 in the inactive state, a free end 26a of the blocking tab 26 is at a distance from the projection 20 of the bottom wall 17 and the top surface 17b of the bottom wall 17 so that the tie 5 can pass through,
- in the closed position of the blocking lever 22 in the active state, the free end 26a of the blocking tab 26 is close to the projection 20 of the bottom wall 17 and the top surface 17*b* of the bottom wall 17 so as to block a portion of the tie 5, the free end 26*a* of the blocking tab 26 forming another blocking portion of the blocking lever.

Figure 4:
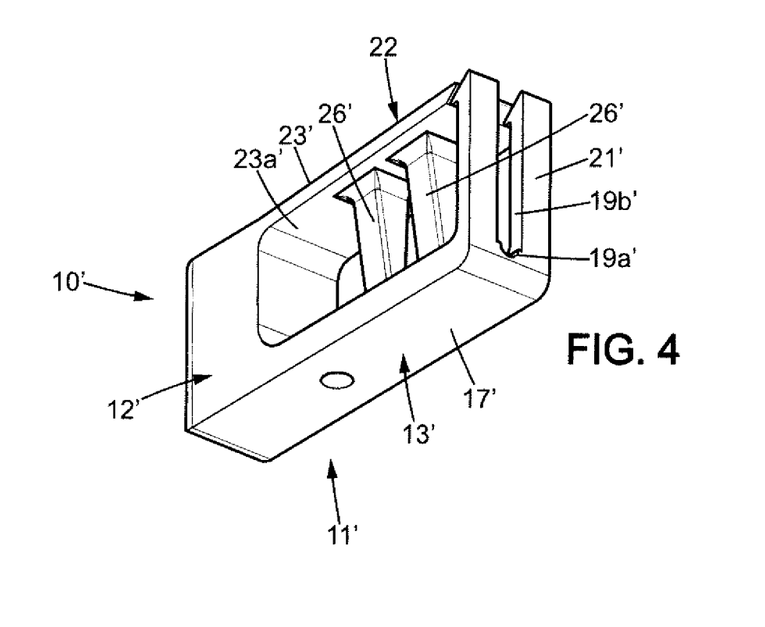
Figure 5:
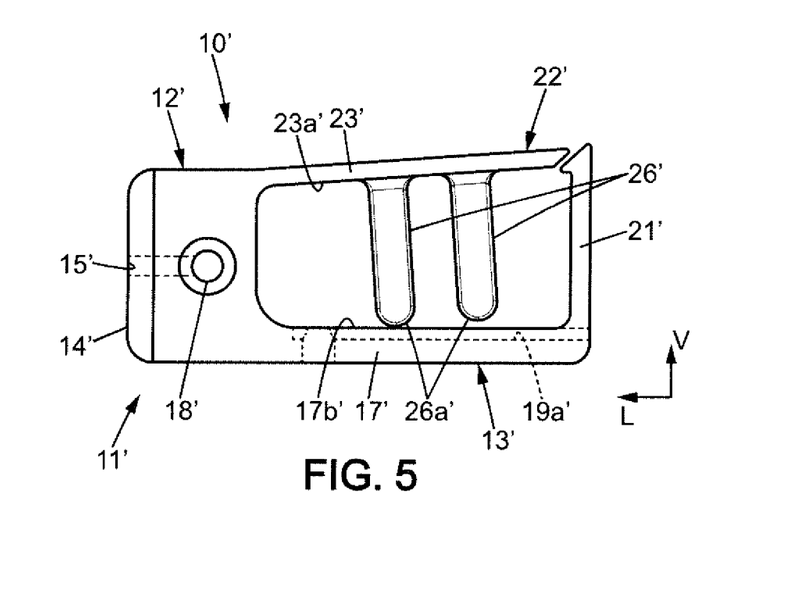

In one variant shown on FIGS. 4 and 5, the tensioner 10' also comprises a body 11' corresponding to the body 11 of the previously described tensioner 10.

The body 11' of the tensioner 10' according to this variant comprises an orifice 15' formed in a transverse end surface 14' of a distal part 12'. The second end 5*b* of the tie 5 is located in the orifice 15' and is held in place by a tightening device installed in a hole 18' on a lateral surface of the distal part 12' of the body 11' so as to be moveable perpendicular to the axis of the orifice 15' between the tightening position and the retracted position described previously.

The proximal part 13' extends along the longitudinal direction L from a surface opposite the end surface 14' of the distal part 12'. On the top surface 17*b*' of the bottom wall 17', it comprises a groove 19*a*' adapted to hold a part of the tie 5 and that opens up in a recess 19*b*' formed over the entire height of the cross wall 21'.

The blocking lever 22', that is also part of the body 11' made of a plastic material, comprises one or several, for example two, blocking tabs 26' that extend perpendicular from the lower surface 23*a*' of the blocking wall 23' facing the top surface 17*b*' of the bottom wall 17' of the proximal part 13' of the body 11'. The blocking tabs 26 are arranged such that:

in the open position of the blocking lever 22' and in the inactive state, the free ends 26*a*' of the blocking tabs 26' are at a distance from the groove 19*a*' in the bottom wall 17' so that a portion of the tie 5 can be placed in the groove 19*a*', in the closed position of the blocking lever 22 in the active state, the free ends 26*a*' of the blocking tab 26' extend into the groove 19' of the bottom wall 17' so as to block a portion of the tie 5 placed in the groove 19*a*', the free ends 26*a*' of the blocking tab 26' forming blocking portions of the blocking lever 22'.

In the embodiment shown, the skin expansion system 1 also comprises one or several spacers 30 designed to be inserted between the tie 5 and the tissues 3 surrounding the wound 2. The spacer 30 is made from any appropriate material to transfer traction applied by the tie 5 on the tissues 3 surrounding the wound 2 and, if necessary, to improve guidance of the tie 5 and facilitate its placement. In particular, the spacer 30 can be made of polymer and in particular silicone, to facilitate its anatomic adaptation to the tissues on which it rests.

Figures 6, 7:
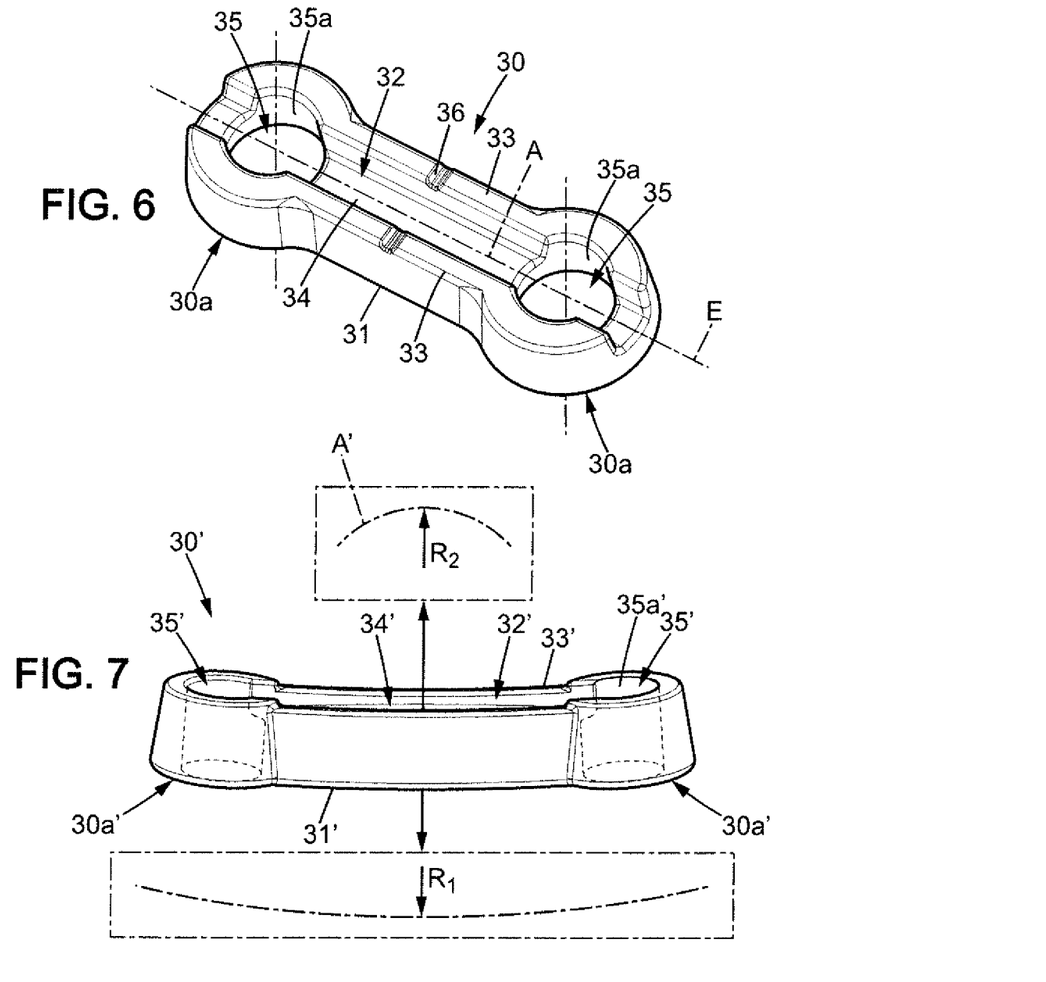
FIG. 6 is a perspective view of a spacer according to a first embodiment that can be used in the skin expansion system of FIG. 1, the spacer being designed to be inserted between the tie and the tissues surrounding the wound.
FIG. 7 is a perspective view of a variant embodiment of the spacer of FIG. 6, FIGS. 8 and 9 are diagrammatic views illustrating placement of the spacer of FIG. 7 on tissues surrounding a wound.

In a first embodiment shown on FIG. 6, the spacer 30 is in the form of a platelet extending along an extension direction E. The spacer 30 has a bearing surface 31 adapted to rest on the tissues 3 surrounding the wound 2, and a guide surface 32 opposite the bearing surface 31 and adapted to receive a portion of the tie 5.

The bearing surface 31 is plane and deprived from any anchor member adapted to pierce the tissues 3 surrounding the wound 2 and penetrate into these tissues 3. In particular, the bearing surface 31 may be smooth. As a variant, still preferably without anchor member, the bearing surface 31 can be curved and/or textured, in other words it is provided with a network of non-perforating projections, to further improve adhesion to a surface of tissues 3 surrounding the wound 2.

The guide surface 32 extends along a guide axis A, an essential part of which is parallel to the extension direction E, and is concave around the guide axis A. In particular, two longitudinal edges 33 parallel to the extension direction E are located on each side of a central portion 34 in recess with respect to the longitudinal edges 33.

The spacer 30 comprises two guide openings 35 arranged approximately at two opposite ends of the spacer 30 and adapted to allow the tie 5 to pass through. The guide openings 35 are connected to each other through the guide surface 32 and have each a lateral surface 35*a*, for example cylindrical, about a central axis. Part of the lateral surface 35*a* of each of the guide openings 35 forms one end of the guide surface 32 of the spacer 30. Between the guide openings 35, for example in an approximately median zone, the spacer 30 has a break-off portion materialised by a groove 36 at which the spacer 30 can be separated into two half-spacers 30*a* each comprising one of the guide openings 35 and part of the bearing surface 31 and the guide surface 32.

Figure 8:
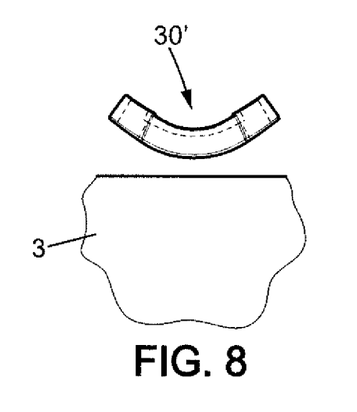
Figure 9:
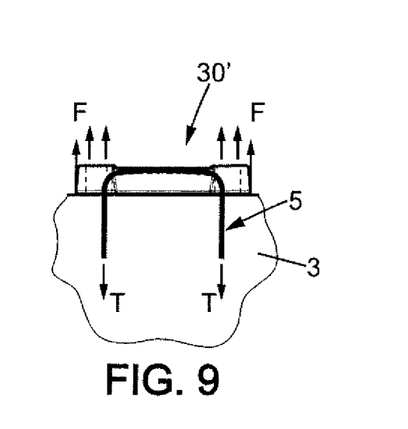

In one variant shown on FIGS. 7 to 9, the spacer 30' is shaped such that when at rest, and when there are no external constraints, the bearing surface 31' has a convexity R1 in the direction opposite to the guide surface 32'. The central portion 34' of the guide surface 32' also has a convexity R2 opposite the bearing surface 31', between the guide openings and the bearing surface 31'.

In this way, when the spacer 30' is positioned on the tissues 3 surrounding the wound 2 and the tie 5 passes between the guide openings 35' on the guide surface 32', the spacer 30' can be deformed to match the anatomical surface of the tissues 3 surrounding the wound 2 applying a resultant force F on the tie 5 opposed to the traction T, resulting in a reduction of stresses on the tissues 3.

Figure 10:
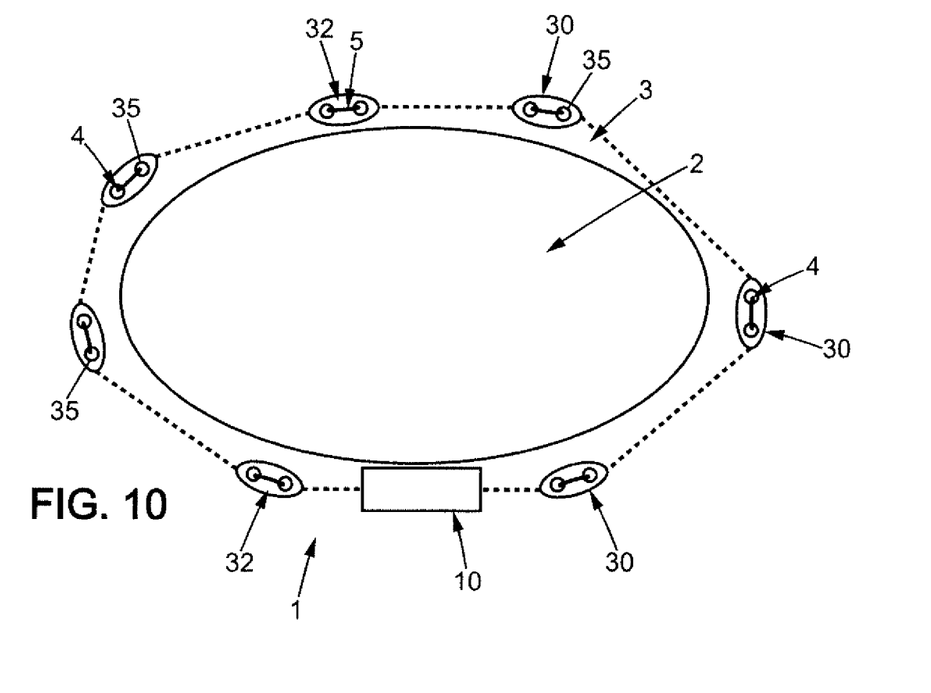
FIG. 10 is a diagrammatic view of a reduction of a wound making use of the skin expansion system of FIG. 1 with several spacers as shown on FIGS. 6 and 7 in a bridge assembly.

FIG. 10 shows one embodiment of the skin expansion system 1 that has just been described in a bridge setup.

The wound 2 is sutured passing the suture needle 6 through the tissues 3 surrounding the wound 2, from underneath, at a first suture point 4 then through one of the guide openings 35 in a first spacer 30 of which the bearing surface 31 lies on the tissues 3 surrounding the wound 2. The suture needle 6 then passes in the other guide opening 35 of the first spacer 30 then through the tissues 3 surrounding the wound 2, from above, at a second suture point 4, the tie 5 thus passing through the guide openings 35 and extending in the central portion 34 of the guide surface 32. This same operation is repeated for a determined number of spacers 30 such that the tie 5 extends around the wound 2, passing under the tissues 3 surrounding the wound 2 between two consecutive spacers 30, and on the guide surface 32 between the two guide openings 35 of each spacer 30.

Once the tie 5 has satisfactorily sutured the wound 2, the suture needle 6 can be separated from the tie 5 and the tie 5 can be inserted into the passage between the blocking lever in the open position and the body 11 of the tensioner 10 to adjust the tension in the tie 5. The orifice 15 retaining the second end 5*b* of the tie 5 and the passage retaining another portion of the tie 5 being arranged on each side of the tensioner 10 along the longitudinal direction L, the tensioner 10 can be located in line with the tie 5 between two consecutive suture points 4.

When a satisfactory tension is obtained, the blocking lever 22 is moved into the closed position to block a portion of the tie 5 at a distance from the second end 5*b* of the tie 5.

Later on, the tension in the tie 5 can be adjusted once again, and in particular increased, by moving the blocking lever 22 into the open position and pulling the tie 5 before putting the blocking lever 22 back into the closed position.

As the tension in the tie 5 increases, the traction on the tissues 3 surrounding the wound 2 increases, thus reducing the wound 2.

The skin expansion system thus forms a dynamic system to reduce a wound 2.

As a variant, the skin expansion system 1 could be used in a similar manner without any spacers 30, the tie 5 suturing the wound directly by passing alternately above and below the tissues 3 surrounding the wound 2 between two consecutive suture points 4. Furthermore, the arrangement of the suture points and possibly the spacers 30 could be different from the arrangement described above.

Figure 11:
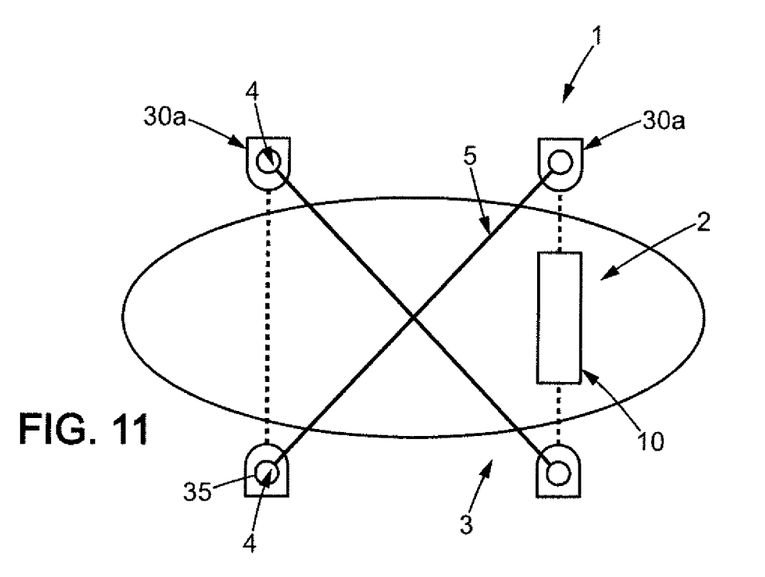
FIG. 11 is a diagrammatic view of a reduction of a wound making use of the skin expansion system of FIG. 1 with several spacers as shown on FIGS. 6 and 7 in a shoelace assembly.

For example, FIG. 11 illustrates one embodiment of the skin expansion system 1 described above in a shoelace setup. In such a setup, the suture points 4 are not joined in sequence around the wound 2 as described above, but instead they are in sequence on either sides of the wound 2, such that portions of the tie 5 extend over the wound 2. Furthermore, on FIG. 6, the spacers 30 have been separated into half-spacers 30a, the bearing surface 31 of one of the half-spacers 30a lying on the tissues 3 surrounding the wound 2 at each suture point 4, the tie 5 passing through the guide opening 35 and extending over part of the guide surface 32 of the half-spacer 30a.

The tension in the tie 5 can be maintained and adjusted as described above, using the tensioner 10.

Figure 12:
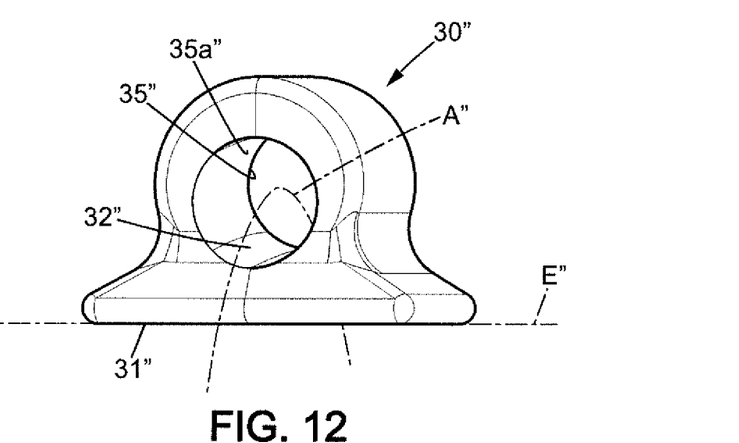
FIG. 12 is a perspective view of a spacer according to a second embodiment that can be used in the skin expansion system of FIG. 1.
Figure 13:
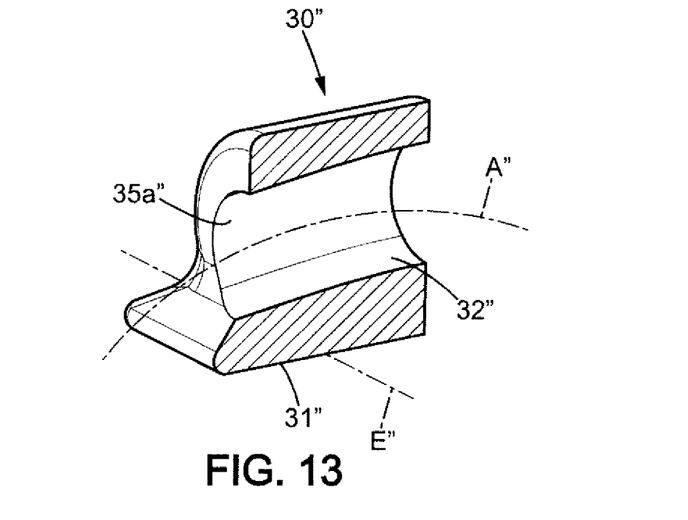
FIG. 13 is a sectional view of the spacer of FIG. 12.

In a second embodiment shown on FIGS. 12 and 13, the spacer 30" is in the form of a stud that also has a bearing surface 31" adapted to rest on the tissues 3 surrounding the wound 2, and a guidance circuit 32" opposite the bearing surface 31" and adapted to receive a portion of the tie 5.

The bearing surface 31" is similar to the bearing surface of the spacer 30 according to the first embodiment.

However, unlike the spacer 30 according to the first embodiment, the spacer 30" according to the second embodiment comprises a single guide opening 35" with a lateral surface 35a" around a central axis curved around an axis of the bearing surface 31" parallel to the extension direction E". The lateral surface 35a" is thus approximately toroidal and comprises the guide surface 32" in the form of hyperbolic paraboloid concave around the central axis forming the guide axis A", and convex around the axis of the bearing surface 31".

The wound 2 is sutured by passing the suture needle 6 through the tissues 3 surrounding the wound 2, from underneath, at a first suture point 4 then through the guide opening 35" in a first spacer 30" of which the bearing surface 31" lies on the tissues 3 surrounding the wound 2. The suture needle 6 then passes through the tissues 3 surrounding the wound 2, from above, at a second suture point 4. This same operation is repeated for a determined number of spacers 30" such that the tie 5 extends around the wound 2 or on the wound 2, passing under the tissues 3 surrounding the wound 2 between two consecutive spacers 30", and on the guide surface 32" of each spacer 30". The tension in the tie 5 can be maintained and adjusted as described above using the tensioner 10.

The invention claimed is:

1. Skin expansion system to reduce a wound surrounded by tissues, the skin expansion system comprising:

only one elastically deformable tie intended to extend between the tissues surrounding the wound in such a way that tension in the tie produces traction along the tissues surrounding the wound in order to bring said tissues closer together, the tie having opposed first and second ends, the tie having at rest a length between the first and second ends and being elastically stretchable to move the first and second ends away from each other, only one tensioner adapted to maintain tension in the tie, wherein the tie is adapted to suture the wound by passing directly through the tissues surrounding the wound at at least two suture points, the tie being made from a biocompatible material and comprising a suture needle rigidly connected to the first end, wherein the skin expansion system also comprise a plurality of spacers, each spacer intended to be inserted between the tie and the tissues surrounding the wound at one of the suture points, each spacer being separate from the tensioner and having a bearing surface adapted to rest on the tissues surrounding the wound, and a guide surface opposite the bearing surface adapted to receive a portion of the tie, wherein the bearing surface is plane and does not have any anchor member adapted to pierce the tissues surrounding the wound and penetrate into these tissues.

2. Skin expansion system according to claim 1, wherein the tie is made of a polymer.

3. Skin expansion system according to claim 1, wherein the tensioner comprises:

a body fixed to the second end of the tie, and a blocking device that can be moved relative to the body between an inactive state in which said blocking device releases a passage for the tie between a blocking portion of said blocking device and the body, and an active state in which said blocking device keeps a portion of the tie at a distance from the second end between the blocking portion of said blocking device and the body.

4. Skin expansion system according to claim 1, wherein each spacer is shaped such that when at rest, the bearing surface has a convexity in the direction opposite to the guide surface.

5. Skin expansion system according to claim 1, wherein the guide surface extends along a guide axis and is concave around the guide axis.

6. Skin expansion system according to claim 1, wherein each spacer comprises at least one guide opening with a lateral surface around a central axis and adapted to enable the tie to pass through, the lateral surface forming at least part of the guide surface.

7. Skin expansion system according to claim 6, wherein spacer comprises at least two guide openings separated from each other by a break-off portion.

8. Skin expansion system according to claim 1, in which each spacer is made of a polymer.

9. Skin expansion system according to claim 1, wherein the tie is made of silicone.

10. Skin expansion system according to claim 1, in which each spacer is made of silicone.

* * * * *